United States Patent [19]
Gorun et al.

[11] Patent Number: 5,099,045
[45] Date of Patent: Mar. 24, 1992

[54] MANGANESE OLIGOMER CONTAINING MAIN GROUP ELEMENTS

[75] Inventors: Sergiu M. Gorun, Upper Montclair; Robert T. Stibrany, Long Valley, both of N.J.

[73] Assignee: Exxon Research and Engineering Company, Florham Park, N.J.

[21] Appl. No.: 698,046

[22] Filed: May 10, 1990

Related U.S. Application Data

[63] Continuation-in-part of Ser. No. 580,413, Sep. 10, 1990, Pat. No. 5,041,575.

[51] Int. Cl.$^5$ .......................... C07F 3/00; C07F 13/00
[52] U.S. Cl. ........................................ 556/28; 556/45; 556/49; 556/50; 423/605
[58] Field of Search ................ 556/28, 45, 49, 50

[56] References Cited

U.S. PATENT DOCUMENTS

| | | | |
|---|---|---|---|
| 4,207,245 | 6/1980 | Halbert | 556/28 |
| 4,730,064 | 3/1988 | Halbert et al. | 556/28 X |
| 4,937,338 | 6/1990 | Flohr et al. | 556/28 X |

Primary Examiner—Arthur C. Prescott
Attorney, Agent, or Firm—Joseph J. Dvorak

[57] ABSTRACT

One embodiment of the present invention is based on the discovery of another hexadecanuclear manganese aggregate having a core of 6 barium ions surrounding a carbonate ion. Stated differently, one embodiment of the present invention comprises a composition of matter having the formula:

$$[Mn_{16}Ba_{10}O_4(OH)_4(CO_3)_5L_8]\cdot xH_2O$$

wherein x is an integer ranging from about 0 to about 120 and L is a ligand.

Another embodiment of the present invention comprises a method of preparing the novel compounds of the present invention, which method comprises preparing a chloride free aqueous solution containing a source of carbonate ion selected from sodium carbonate, $CO_2$ and mixtures thereof and a compound having the formula:

$$Ba_2[Mn_4(O)(OH)(O_2CR)_8L_2]\cdot xH_2O$$

wherein R is hydrogen or a hydrocarbyl group, x is an integer ranging from 0 to about 30, and L is a ligand having formula I set forth above, and thereafter allowing the reaction mixture to stand for a time sufficient for a compound having the formula:

$$[Mn_{16}Ba_{10}O_4(OH)_4(CO_3)_5L_8]\cdot xH_2O$$

to form.

The compounds of the present invention have magnetic properties rendering them particularly suitable for use in magnetic thermometry and magnetic fluids.

11 Claims, 2 Drawing Sheets

MANGANESE OLIGOMER CONTAINING MAIN GROUP ELEMENTS

This is a continuation-in-part of Ser. No. 580,413, filed Sept. 10, 1990, now U.S. Pat. No. 5,041,575.

FIELD OF THE INVENTION

This invention relates to novel compositions of matter and their method of preparation. More specifically, this invention relates to novel compounds including 16 manganese ions and a core of 6 barium ions and a carbonate ion.

BACKGROUND OF THE INVENTION

In copending application Ser. No. 541,699, filed June 21, 1990 now U.S. Pat. No. 5,025,101, there is disclosed a composition of matter having the formula $M_2[Mn_4(O)(OH)(O_2CR)_2L_2]$ wherein M is an alkali earth metal selected from magnesium, calcium, strontium, barium or mixtures thereof, R is hydrogen or a hydrocarbyl group, and L is a ligand having the formula:

$$\begin{array}{c}^-OOCCH_2\\ \phantom{xx}\diagdown\\ \phantom{xxxx}N-CH_2-\underset{\underset{H}{|}}{\overset{\overset{O^-}{|}}{C}}-CH_2-N\\ \phantom{xx}\diagup\phantom{xxxxxxxxxxxxxxxxxx}\diagdown\\ ^-OOCCH_2\phantom{xxxxxxxxxxxxxx}CH_2COO^-\end{array} \quad (I)$$

$$\begin{array}{c}\phantom{^-OOCCH_2xxxxxxxxxxx}CH_2COO^-\\ \phantom{xxxxxxxxxxxxxxxxxx}\diagup\end{array}$$

These compounds have been shown to have a core structure of 4 manganese atoms which are bridged by oxo and hydroxo groups and, hence, they are referred to as oxo (hydroxo) bridged tetranuclear manganese compounds.

In copending application Ser. No. 580,413, filed Sept. 10, 1990 now U.S. Pat. No. 5,041,575, there is disclosed the conversion of the aforementioned oxo (hydroxo) bridged tetranuclear compounds into a hexadecanuclear manganese aggregate having the formula:

$$[Mn_{16}Ba_8Na_2ClO_4(OH)_4(CO_3)_4(H_2O)_{22}L_8] \cdot xH_2O$$

wherein x is an integer ranging from 0 to about 32 and L is the ligand, (I), shown above.

SUMMARY OF THE INVENTION

The present invention is based on the discovery of another hexadecanuclear manganese aggregate having a core of 6 barium ions surrounding a carbonate ion. Stated differently, one embodiment of the present invention comprises a composition of matter having the formula:

$$[Mn_{16}Ba_{10}O_4(OH)_4(CO_3)_5L_8] \cdot xH_2O$$

wherein x is an integer ranging from about 0 to about 120 and L is the ligand, I, shown above.

Another embodiment of the present invention comprises a method of preparing the novel compounds of the present invention, which method comprises preparing a chloride free aqueous solution containing a source of carbonate ion selected from sodium carbonate, $CO_2$ and mixtures thereof and a compound having the formula:

$$Ba_2[Mn_4(O)(OH)(O_2CR)_2L_2] \cdot xH_2O$$

wherein R is hydrogen or a hydrocarbyl group, x is an integer ranging from 0 to about 30, and L is a ligand having formula I set forth above, and thereafter allowing the reaction mixture to stand for a time sufficient for a compound having the formula:

$$[Mn_{16}Ba_{10}O_4(OH)_4(CO_3)_5L_8] \cdot xH_2O$$

to form.

The compounds of the present invention have magnetic properties rendering them particularly suitable for use in magnetic thermometry and magnetic fluids.

DETAILED DESCRIPTION OF THE INVENTION

The compounds of the present invention have the formula:

$$[Mn_{16}Ba_{10}O_4(OH)_4(CO_3)_5L_8] \cdot xH_2O$$

wherein x is an integer indicating the amount of water of crystallization, and as such, may vary over a broad range; for example, in the range of 0 to about 120, and L is a ligand having formula I set forth above. Preferably, x is an integer in the range of from about 70 to about 110.

Figure 1:
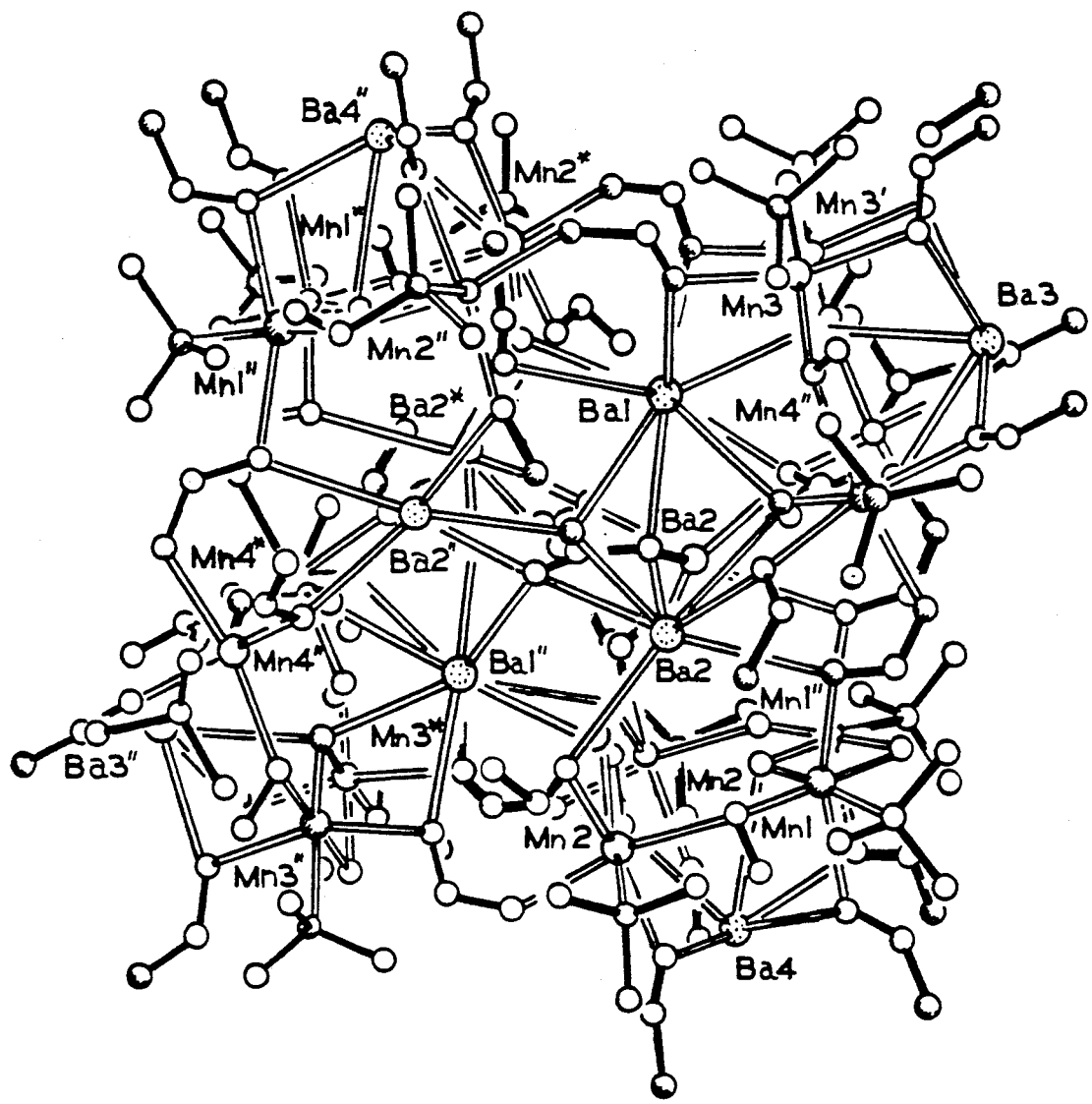
FIG. 1 is a perspective illustration of the structural arrangement of a novel compound of the present invention in which, for purposes of clarity, hydrogen atoms have been omitted; non-hydrogen atoms have been represented by arbitrary-sized spheres; the bonds between Mn, Ba and their coordinated atoms are represented by double lines. Covalent bonds between carbon, hydrogen and oxygen atoms are represented by solid lines.
Figure 2:
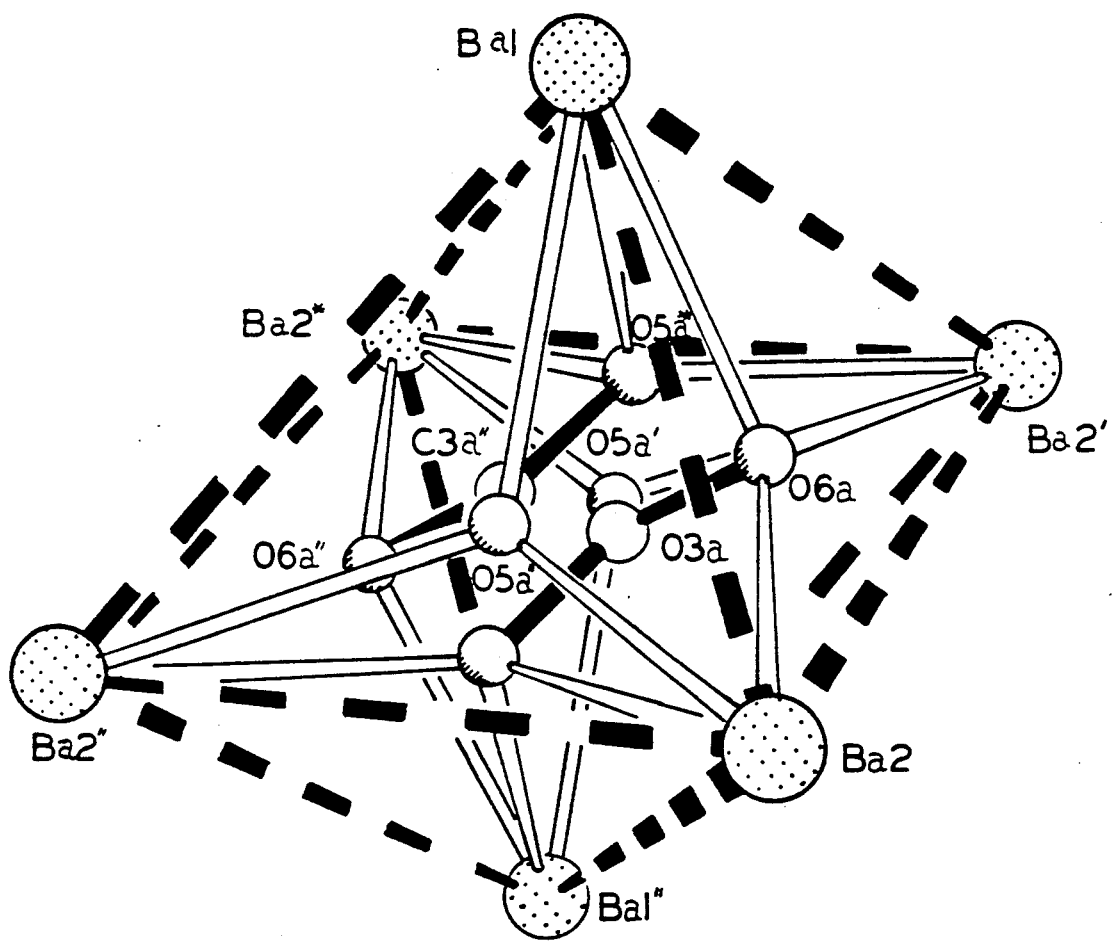
FIG. 2 is a perspective illustration of the central $[Ba_6CO_3]$ core of the compound of FIG. 1. The 6 barium ions describe an octahedral cage defined by dashed solid lines. The central carbonate ion is disordered over two positions within the barium cage.

As is shown in FIGS. 1 and 2, these novel compounds have a core structure of 6 barium ions surrounding a carbonate ion. The barium ions are referred to as main group elements. This main group element core is surrounded by 16 manganese.

The structure of the compounds of the present invention has been determined by well-known single crystal x-ray diffraction techniques.

The compounds of the present invention are prepared by combining a chloride free aqueous solution of a source of carbonate ion, such as sodium carbonate or carbon dioxide, and a compound having the formula:

$$Ba_2[Mn_4(O)(OH)(O_2CR)_2L_2] \cdot xH_2O$$

wherein R is hydrogen or a hydrocarbyl group, especially alkyl, aryl and aralkyl groups and, preferably, R is an alkyl group having from 1 to about 30 carbon atoms. More preferably, R has from 1 to about 10 carbon atoms, and when R is an aralkyl group, it preferably will have from 7 to about 10 carbon atoms. L is a ligand having the formula (I) shown previously, and x is an integer of from 0 to about 30.

The mole ratio of the tetranuclear manganese compound to carbonate source used generally will be in the range of from about 1 to 100 and, preferably, in the range of from about 2 to about 10. When $CO_2$ is the carbonate source, the $CO_2$ can be bubbled through the solution for a time sufficient to assure a large excess of $CO_2$ having been present.

It should be readily appreciated that the tetranuclear compound can be prepared and used in situ and that it is not necessary to first prepare and isolate the tetranuclear compound.

The temperature at which the combined solution is maintained is not critical. Indeed, temperatures of from about 0° C. to about 150° C. may be used, but it is most convenient and preferred to combine the reactants in water at ambient room temperature, and maintain the mixture at that temperature.

The combined solution is then allowed to stand for a time sufficient for the formation of the desired compound. Typically, crystals of the compounds of the present invention form after the combined solution has been allowed to stand overnight. Alternatively, crystallization can be hastened by known techniques such as reducing the volume of solvent by evaporation, seeding the liquid phase and the like.

The crystalline hexadecanuclear manganese compound is readily separated from the aqueous solution by decantation or filtration. The value of x in the product compound, i.e., the amount of water of hydration, will, of course, depend on the extent of drying of the product. Consequently, x will vary broadly; for example, from about 0 to about 120.

The tetranuclear manganese complex used in preparing the novel compound of the present invention is prepared by combining an aqueous containing solution of the compound having the formula:

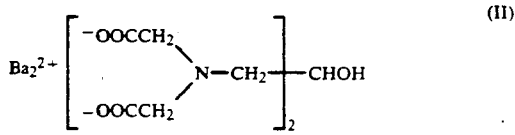

with manganese (II) carboxylate, $Mn(O_2CR)_2$, or a water-soluble manganese (II) salt and a source of carboxylate $RCO_2-$ in which R is hydrogen or a hydrocarbyl group and thereafter oxidizing the mixture to form the tetranuclear manganese compound. Exemplary hydrocarbyl groups for R include alkyl groups, aryl groups and aralkyl groups, and when R is an alkyl group, it will generally have from about 1 to 30 carbon atoms and, preferably, from 1 to 10 carbon atoms. When R is an aralkyl group, it will generally have from about 7 to about 10 carbon atoms.

Exemplary manganese (II) salts suitable for use in preparing the tetranuclear manganese compound include manganese chloride, manganese bromide, manganese nitrate, manganese tetrafluoroborate and manganese sulfate.

Exemplary sources of carboxylate include carboxylic acids and alkali metal salts of carboxylic acids.

Among suitable aqueous solutions are water, water-alcohol and water-dimethyl formamide mixtures. In general, it is particularly preferred to use water as the solvent in the preparation of the tetranuclear manganese complex.

The mole ratio of the barium compound (formula II above) to manganese (II) carboxylate or manganese (II) salt generally will be in the range of about 1:1 to about 1:3 and, preferably, about 1:2.

The hexadecanuclear manganese compounds of the present invention have a magnetic susceptibility above 100° K., which follows the Curie-Weiss law with $\theta = -7°$ K. This magnetic property renders the compounds of the present invention eminently suitable for use in magnetic thermometry and in magnetic fluids.

EXAMPLES

In the examples which follow, DHPTA refers to 1,3-diamino-2-hydroxypropane-N,N,N,N,-tetraacetic acid, the deprotonated form of which is shown as formula I and is referred to as "L".

EXAMPLE 1

In a 50 ml Erlenmeyer flask, 268 mg of DHPTA were added to 20 ml of $H_2O$ and stirred. The pH was brought to 7 with $Ba(OH)_2 \cdot 8H_2O$. Then, 430 mg of $Mn(OAc)_2 \cdot 4H_2O$ were added with 1 ml of methanol and stirred until dissolved. After the pH was brought to 8.0 with $Ba(OH)_2 \cdot 8H_2O$, 1 ml of 30% $H_2O_2$ was added dropwise, giving off heat and gas. The solution was filtered. The filtrate was placed in a 50 ml Erlenmeyer flask, to which 100 mg of $Na_2CO_3$ were added. Overnight, large green crystals formed, which were characterized by x-ray crystallography and elemental analysis. Calculated for $[Mn_{16}Ba_{10}O_4(OH)_4(CO_3)_5L_8] \cdot 92H_2O$: C 16.24%; H 4.28%; N 3.26%. Found: C 15.98%; H 4.21%; N 3.22%.

EXAMPLE 2

In a 50 ml Erlenmeyer flask, 268 mg of DHPTA were added to 20 ml of $H_2O$ and the mixture was stirred. The pH was brought to 7 with $Ba(OH)_2 \cdot 8H_2O$. Then, 430 mg of $Mn(OAc)_2 \cdot 4H_2O$ were added with 1 ml of methanol and stirred until dissolved. After the pH was brought to 8.0 with $Ba(OH)_2 \cdot 8H_2O$, 1 ml of 30% $H_2O_2$ was added dropwise, giving off heat and gas. The solution was filtered. The filtrate was placed in a 50 ml Erlenmeyer flask containing 50 mg of solid $Ba(OH)_2 \cdot 8H_2O$. The $CO_2$ was bubbled into the solution for two hours. Overnight, large green crystals formed, which were identical to those obtained using the procedure in Example 1.

What is claimed is:

1. A composition of matter having the formula:

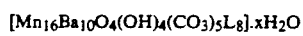

wherein x is an integer ranging from 0 to about 120 and L is a ligand having the formula:

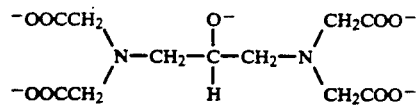

2. The composition of claim 1 wherein x is in the range of from about 70 to about 110.

3. The composition of claim 1 wherein x is 92.

4. The composition of claim 1 wherein the 16 manganese ions surround a core of the 6 barium ions, which surround a carbonate ion.

5. A hexadecanuclear manganese aggregate including a core of 6 barium ions and 5 carbonate ions in which the core is surrounded by 16 manganese ions.

6. A method for preparing a compound having the formula:

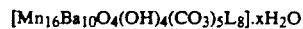

wherein x is an integer of from 0 to about 120 and L is a ligand having the formula:

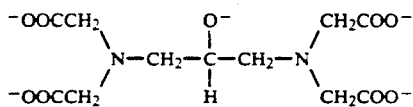

comprising:

forming a chloride free aqueous solution containing a source or $CO_3^=$ and a compound having the formula:

$Ba_2[Mn_4(O)(OH)(O_2CR)_2L_2] \cdot xH_2O$ wherein R is hydrogen or a hydrocarbyl group, x is an integer ranging from 0 to about 30, and L is a ligand having the formula above;

allowing the solution to stand for a time sufficient for the compound to form.

7. The method of claim 6 wherein the source of $CO_3^=$ is selected from the group consisting of $Na_2CO_3$, $CO_2$ and mixtures thereof.

8. The method of claim 7 wherein the mole ratio of $Ba_2[Mn_4(O)(OH)(O_2CR)_2L_2] \cdot xH_2O$ to $CO_3^=$ is in the range of from about 1 to about 100.

9. The method of claim 8 wherein the mole ratio of $Ba_2[Mn_4(O)(OH)(O_2CR)_2L_2] \cdot xH_2O$ to $CO_3^=$ source is in the range of from about 2 to about 10.

10. The method of claim 9 wherein the $Ba_2[Mn_4(O)(OH)(O_2CR)_2L_2] \cdot xH_2O$ compound is prepared in situ.

11. The method of claim 9 wherein the $Ba_2[Mn_4(O)(OH)(O_2CR)_2L_2] \cdot xH_2O$ is prepared, separated and then combined with the source of $CO_3^=$.

* * * * *